United States Patent
Duffy et al.

(10) Patent No.: US 11,154,389 B2
(45) Date of Patent: Oct. 26, 2021

(54) ASSEMBLIES AND METHODS OF STERILIZING A WET STORED IMPLANT

(71) Applicant: Medtronic Vascular, Inc., Santa Rosa, CA (US)

(72) Inventors: Niall Duffy, Galway (IE); Stephen Montgomery, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 272 days.

(21) Appl. No.: 16/404,805

(22) Filed: May 7, 2019

(65) Prior Publication Data
US 2019/0336262 A1 Nov. 7, 2019

Related U.S. Application Data

(60) Provisional application No. 62/667,771, filed on May 7, 2018.

(51) Int. Cl.
| | |
|---|---|
| *A61F 2/00* | (2006.01) |
| *A61F 2/24* | (2006.01) |
| *A61L 2/18* | (2006.01) |
| *A61L 2/08* | (2006.01) |
| *A61L 2/16* | (2006.01) |
| *A61L 2/20* | (2006.01) |

(52) U.S. Cl.
CPC ............ *A61F 2/0095* (2013.01); *A61L 2/087* (2013.01); *A61L 2/16* (2013.01); *A61L 2/206* (2013.01); *A61F 2/2427* (2013.01); *A61L 2202/21* (2013.01)

(58) Field of Classification Search
CPC ...... A61F 2/0095; A61F 2/24; A61L 2202/21; A61L 2/18
See application file for complete search history.

(56) References Cited

U.S. PATENT DOCUMENTS

| | | | |
|---|---|---|---|
| 2005/0278012 A1* | 12/2005 | Vonderwalde | A61L 2/081 623/1.11 |
| 2013/0118949 A1 | 5/2013 | Chang et al. | |
| 2017/0325928 A1 | 11/2017 | Ino et al. | |

OTHER PUBLICATIONS

The International Search Report and Written Opinion for International Application No. PCT/US2019/031035 dated Jul. 11, 2019 (11 pgs.).

* cited by examiner

*Primary Examiner* — Kevin Joyner
(74) *Attorney, Agent, or Firm* — Dicke, Billig & Czaja, PLLC (57) ABSTRACT

Aspects of the disclosure relate to "wet" transcatheter prosthetic heart valve or other implant packaging and assemblies in which a prosthetic heart valve or other implant is loaded into a first portion of a delivery device and positioned within a container in which sterilizing fluid is retained to sterilize inside of the container as well as provide moisture to prevent the implant from drying out. The disclosure also relates to methods of sterilizing the disclosed assemblies. Some disclosed methods include at least two sterilizing steps and adjustment of a shaft seal or formation of multiple seals maintaining sterilizing fluid within the container so that areas underneath the shaft seal(s) can also be sterilized.

20 Claims, 7 Drawing Sheets

ASSEMBLIES AND METHODS OF STERILIZING A WET STORED IMPLANT

CROSS-REFERENCE TO RELATED APPLICATION

This Non-Provisional Patent Application claims the benefit of the filing date of U.S. Provisional Patent Application Ser. No. 62/667,771, filed May 7, 2018, the entire teachings of which are incorporated herein by reference.

FIELD OF THE DISCLOSURE

Disclosed embodiments relate to packaging for a "wet" tissue prosthetic heart valve or other implant with at least a portion of a delivery device. Methods of assembling packaged transcatheter prosthetic heart valves or implants with the portion of the delivery device and sterilizing the same are also disclosed.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter of a delivery device, inserted inside a body lumen of the patient, such as the femoral artery, and delivered to a desired location in the heart where the valve prosthesis is then deployed.

Known valve prostheses include a stent frame supporting a valve structure. The valve structure can assume a variety of forms, and can be formed, for example, from tissue made from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. The valve structure can be formed from heart valve tissue, pericardium, and/or other suitable tissue. In some embodiments, the valve structure can include or form one or more leaflets. For example, the valve structure can be in the form of a tri-leaflet bovine pericardium valve, a bi-leaflet valve, or another suitable valve.

A valve prosthesis is often packaged in a container filled with solution, such as glutaraldehyde, for sterilizing and preserving the valve prosthesis prior to attachment to a delivery device for delivery to a patient. Such a method is generally referred to as a "wet" stored valve. Sometimes, the valve prosthesis is preloaded on a distal portion of the delivery device, which are both packaged in the container. Some known packaging configurations include both wet and dry compartments; wherein the valve prosthesis is stored in a wet compartment loaded onto the delivery device component and the remainder of the delivery device component is secured in a dry compartment.

The disclosed embodiments address problems and limitations with the related art.

SUMMARY

Aspects of the disclosure relate to "wet" transcatheter prosthetic heart valve or other implant packaging and assemblies in which a prosthetic heart valve or other implant is loaded into a first portion of a delivery device and positioned within a container in which sterilizing fluid is retained to sterilize interior portions of the container as well as provide moisture to prevent the implant from drying out. The disclosure also relates to methods of sterilizing the disclosed assemblies. Some disclosed methods include at least two sterilizing steps and adjustment of a mechanical seal member (i.e. formation of multiple seals) maintaining sterilizing fluid within the container so that areas proximate the seal member(s) can also be sterilized.

Various disclosed assemblies include a first portion of a delivery device supporting an implant. The assemblies further include a container housing sterilization fluid, the implant and at least a portion of the first portion of the delivery device. The container includes an opening and a seal positioned in the opening and adjacent the first portion of the delivery device so that the sterilization fluid is sealed within the container. In addition, the assemblies include a positioning apparatus that is configured to move the container from a first position on the first portion of the delivery device to a second position on the first portion of the delivery device. The positioning apparatus can be of many configurations suitable for selectively or automatically moving the container along the first portion of the delivery device. Optionally, the assembly further includes a sealed pouch and a tray to house the first portion of a delivery device, container and implant for storage and transport.

Various methods of sterealizing the disclosed assemblies include the step of providing one of the disclosed assemblies and conducting a dry sterilization process when the container is in a first position with respect to the first portion of the delivery device. Then the method includes actuating the positioning apparatus to move the container along the first portion of the delivery device into the second position to subsequently sterilize the area proximate the position of the seal member in the first position. Actuation of the positioning apparatus can be manual or automatic. The subsequent sterilization of the assembly can be conducted via the sterilization fluid within the container or via additional dry sterilization techniques depending on whether the second position of the container is proximal or distal with respect to the first position.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted prosthetic heart valve, the terms "distal" and "outflow" are understood to mean downstream to the direction of blood flow, and the terms "proximal" or "inflow" are understood to mean upstream to the direction of blood flow.

As referred to herein, implants useful with and/or as part of the various assemblies, devices and methods of the present disclosure may assume a wide variety of different configurations, such as a stented transcatheter prosthetic heart valves including a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valves useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., nitinol). The stent frame can be laser-cut from a single piece of material, or can be assembled from a number of discrete components.

Figure 1A:
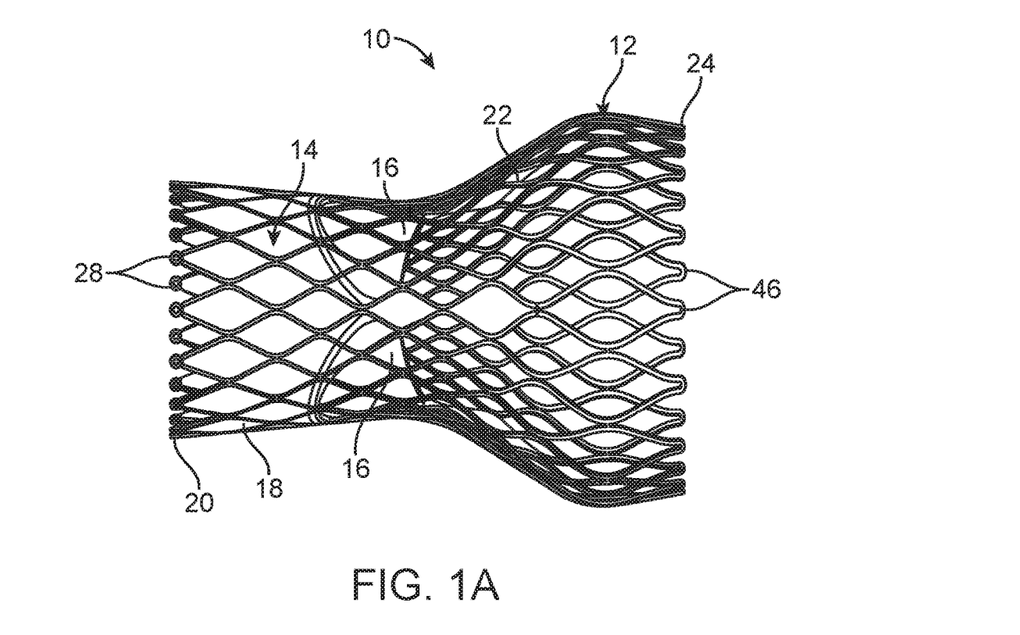
FIG. 1A is a side view of a stented prosthetic heart valve useful with assemblies, devices and methods of the present disclosure and in a normal, expanded condition.
Figure 1B:
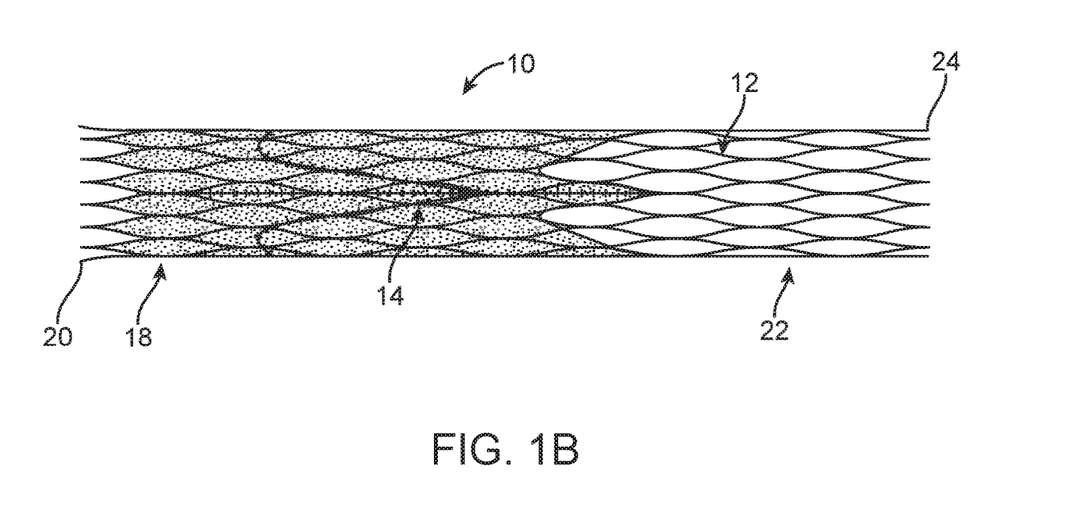
FIG. 1B is a side view of the prosthetic heart valve of FIG. 1A in a compressed condition.

With the above understanding in mind, one simplified, non-limiting example of an implant 10, a stented prosthetic heart valve, useful with systems, devices and methods of the present disclosure is illustrated in FIGS. 1A-1B. As a point of reference, the prosthetic heart valve 10 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 10 includes a stent or stent frame 12 and a valve structure 14. A paravalvular leakage prevention wrap (not shown) can optionally be provided around the stent frame 12. The stent frame 12 can assume any of the forms mentioned above, and is generally constructed so as to be self-expandable, balloon-expandable, and/or mechanically expandable from the compressed condition (FIG. 1B) to the normal, expanded condition (FIG. 1A). In some embodiments, the stent frame can be self-expandable, balloon expandable or mechanically expandable or combinations thereof.

The valve structure 14 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 14 can be formed, for example, from bovine, porcine, equine, ovine and/or other suitable animal tissues. In some embodiments, the valve structure 14 can be formed, for example, from heart valve tissue, pericardium, and/or other suitable tissue. In some embodiments, the valve structure 14 can include or form one or more leaflets 16. For example, the valve structure 14 can be in the form of a tri-leaflet valve, a bi-leaflet valve, or another suitable valve. In some constructions, the valve structure 14 can comprise two or three leaflets that are fastened together at enlarged lateral end regions to form commissural joints, with the unattached edges forming coaptation edges of the valve structure 14. The leaflets 16 can be fastened to a skirt that in turn is attached to the frame 12. The upper ends of the commissure points can define an inflow portion 18 corresponding to a first or inflow end 20 of the prosthetic heart valve 10. The opposite end of the valve can define an outflow portion 22 corresponding to a second or outflow end 24 of the prosthetic heart valve 10. As shown, the stent frame 12 can have a lattice or cell-like structure, and optionally forms or provides crowns 26 and/or eyelets 28 (or other shapes) at the outflow and inflow ends 20, 24.

With the one exemplary construction of FIGS. 1A and 1B, the prosthetic heart valve 10 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve or compassionate use such as heterotopic implants).

Figure 2A:
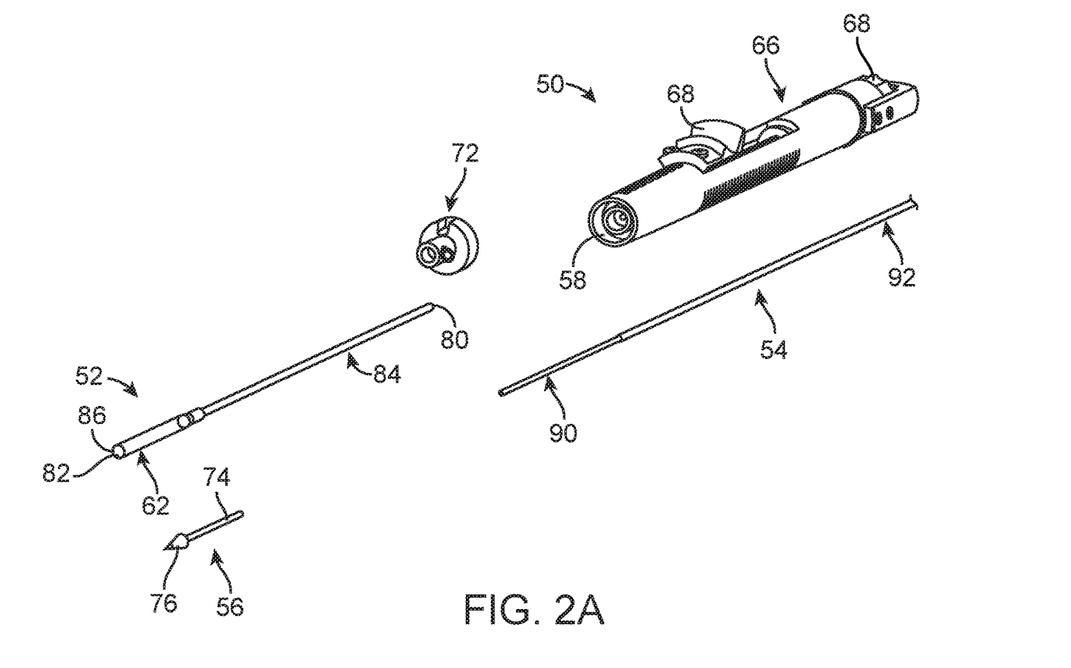
FIG. 2A is an exploded perspective view of a delivery device in accordance with principles of the present disclosure.
Figure 2B:
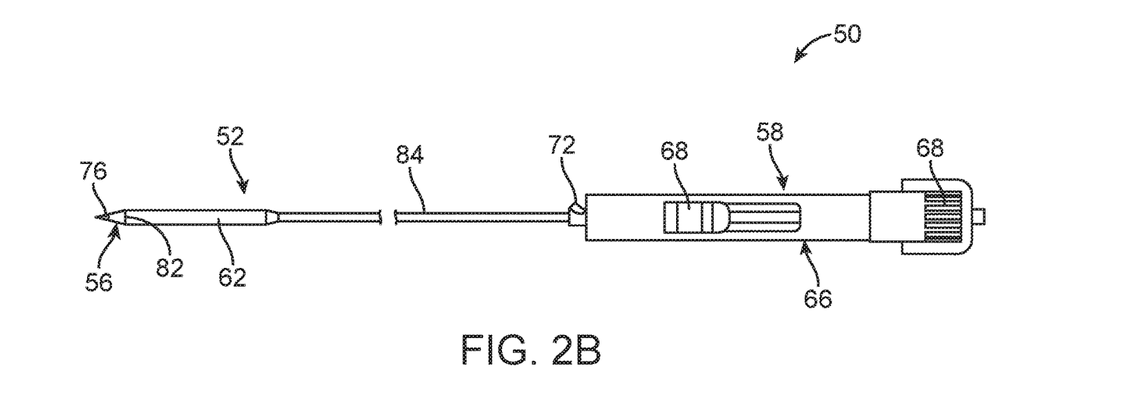
FIG. 2B is an assembled top view of the delivery device of FIG. 2A.

With the above understanding of some example implant valves in mind, one embodiment of a delivery device 50 for percutaneously delivering the implant is shown in simplified form in FIGS. 2A and 2B. The delivery device 50 includes an optional delivery sheath assembly 52, a shaft assembly 54 having a spindle 56 and a handle assembly 58. Details on the various components are provided below. In general terms, however, the delivery device 50 combines with an implant (e.g., the prosthetic heart valve of FIGS. 1A-1B) to form a system for performing a therapeutic procedure. The delivery device 50 provides a loaded or delivery state in which the implant is loaded over the spindle 56 and is compressively retained within a capsule 62 of the delivery sheath assembly 52. The delivery sheath assembly 52 can be manipulated to withdraw the capsule 62 proximally from over the prosthetic heart valve via operation of the handle assembly 58, permitting the prosthetic heart valve to self-expand and partially release from the spindle 56. When the capsule 62 is retracted proximally, the implant can completely release or deploy from the delivery device 50. The delivery device 50 can optionally include other components that assist or facilitate or control complete deployment of the implant, as desired.

Various features of the components 52-58 reflected in FIGS. 2A and 2B and as described below can be modified or replaced with differing structures and/or mechanisms. Thus, the present disclosure is in no way limited to the delivery sheath assembly 52, the shaft assembly 54 or the handle assembly 58 as shown and described below. Further, the delivery device 50 can optionally include additional components or features, such as a flush port assembly 72, a recapture sheath (not shown), etc.

In some embodiments, the optional delivery sheath assembly 52 defines proximal and distal ends 80, 82, and includes the capsule 62 and an outer shaft 84. The delivery sheath assembly 52 can be akin to a catheter, defining a lumen 86 (referenced generally) that extends from the distal end 82 through the capsule 62 and at least a portion of the outer shaft 84. The lumen 86 can be open at the proximal end 80 (e.g., the outer shaft 84 can be a tube). The capsule 62 extends distally from the outer shaft 84, and in some embodiments has a more stiffened construction (as compared to a stiffness of the outer shaft 84) that exhibits sufficient radial or circumferential rigidity to overtly resist the expected expansive forces of the implant (not shown) when compressed within the capsule 62. For example, the outer shaft 84 can be a polymer tube embedded with a metal braiding, whereas the capsule 62 includes a laser-cut metal tube that is optionally embedded within a polymer covering. Alternatively, the capsule 62 and the outer shaft 84 can have a more uniform or even homogenous construction (e.g., a continuous polymer tube). Regardless, the capsule 62 is constructed to compressively retain the stented prosthetic heart valve at a predetermined diameter when loaded within the capsule 62, and the outer shaft 84 serves to connect the capsule 62 with the handle assembly 58. The outer shaft 84 (as well as the capsule 62) is constructed to be sufficiently flexible for passage through a patient's vasculature, yet exhibits sufficient longitudinal rigidity to effectuate desired axial movement of the capsule 62. In other words, proximal retraction of the outer shaft 84 is directly transferred to the capsule 62 and causes a corresponding proximal retraction of the capsule 62. In other embodiments, the outer shaft 84 is further configured to transmit a rotational force or movement onto the capsule 62.

The shaft assembly 54 can have various constructions appropriate for supporting the delivery sheath assembly 52 and an implant relative to the capsule 62. In some embodiments, the inner shaft assembly 54 includes an intermediate shaft or tube 90 and a proximal shaft or tube 92. The intermediate tube 90 is optionally formed of a flexible polymer material (e.g., PEEK), and is sized to be slidably received within the delivery sheath assembly 52. The intermediate tube 90 serves as a transition to the deflection assembly 60, and in some embodiments is a flexible polymer tubing (e.g., PEEK) having a diameter slightly less than that of the proximal tube 92. The proximal tube 92 can have a more rigid construction, configured for robust assembly with the handle assembly 58, such as a metal hypotube. Other constructions are also envisioned. For example, in other embodiments, the intermediate and proximal tubes 90, 92 are integrally formed as a single, homogenous tube or shaft. Regardless, the inner shaft assembly 54 forms or defines at least one lumen (not shown) sized, for example, to slidably receive a guide wire (not shown).

The spindle 56 of the inner shaft assembly 54 includes an inner support shaft 74 and a tip 76. The inner support shaft 74 is sized to be slidably received within the lumen 86 of the delivery sheath assembly 52, and is configured for mounting to the deflection assembly 60. The inner support shaft 74 can be a flexible polymer tube embedded with a metal braid. Other constructions are also acceptable so long as the inner support shaft 74 exhibits sufficient structural integrity to support a loaded, compressed stented prosthetic heart valve (not shown). The tip 76 forms or defines a nose cone having a distally tapering outer surface adapted to promote atraumatic contact with bodily tissue. The tip 76 can be fixed or slidable relative to the inner support shaft 74. The spindle 56 can define a continuous lumen (not shown) sized to slidably receive an auxiliary component such as a guide wire (not shown).

The handle assembly 58 generally includes a housing 66 and one or more actuator mechanisms 68 (referenced generally). The housing 66 maintains the actuator mechanism(s) 68, with the handle assembly 58 configured to facilitate sliding movement of the delivery sheath assembly 52 relative to other components (e.g., the inner shaft assembly 54, the spindle 56. The housing 66 can have any shape or size appropriate for convenient handling by a user.

With the above general explanations of exemplary embodiments of the components of the delivery device 50 in mind, the present disclosure provides many assemblies for storing implants in a "wet" (generally submerged within sterilization fluid) state with at least a portion of a delivery device (e.g., an inner shaft assembly or spindle of a delivery, device such as the delivery device 50). The disclosed embodiments are configured to allow for sterilization of the implant and portions of the delivery device included in the assembly. In the embodiments disclosed herein, the implants can either be stored in either the expanded or compressed condition.

Figure 3:
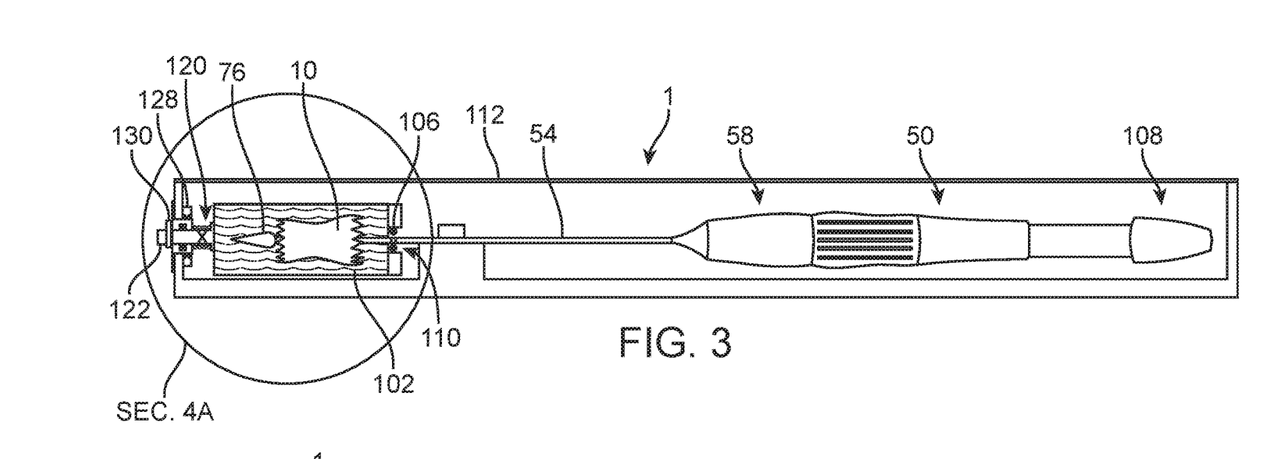
FIG. 3 is schematic illustration of an assembly in a first position.
Figure 4A:
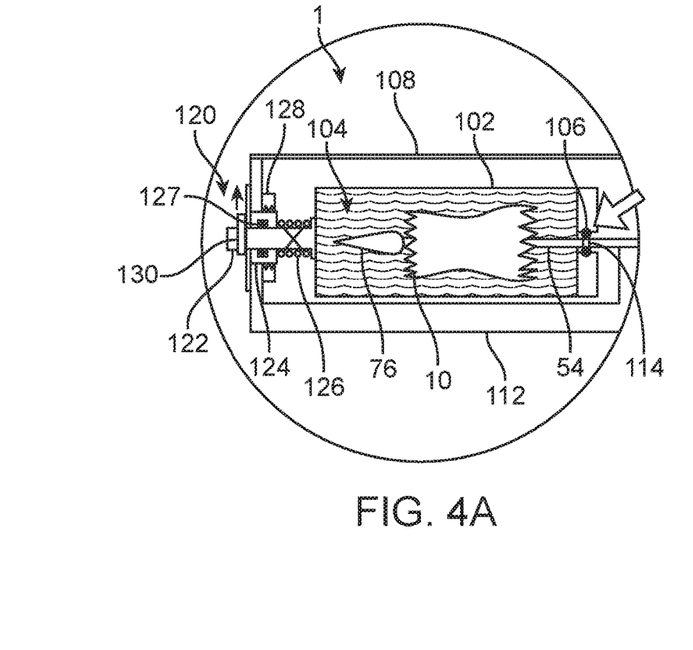
FIG. 4A is an enlarged view of Section 4A of FIG. 3.
Figure 4B:
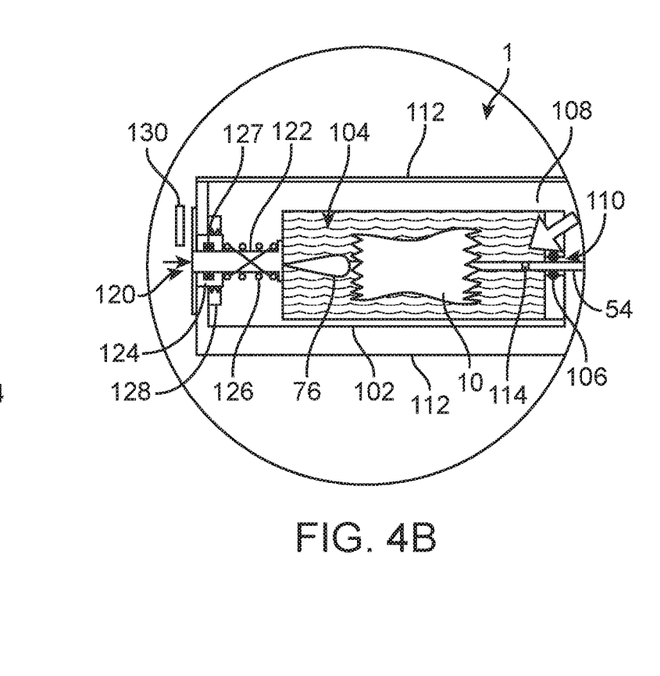
FIG. 4B is an enlarged view of Section 4A of the assembly in a second position.

When preloading an implant to a delivery device for storage prior to use, it is often desired to store the implant "wet" (i.e. with sterilization fluid such as gluteradldehyde) and most of a delivery device "dry" (i.e. without contact of sterilization fluid). One embodiment of an assembly 1 for wet storage of an implant and dry storage of a delivery device is schematically illustrated in FIGS. 3-4B. The assembly 1 includes the implant 10 preloaded onto the shaft assembly 54 of the delivery device 50. It will be understood that the implant 10 and delivery device 50 are merely provided as examples that that the disclosure is not intended to be limited to any specific implant or delivery device. Further, in this embodiment, the implant 10 is loaded onto and packaged with a complete delivery device 50, however, not all of the delivery device 50 is required as part of the assembly 1. For example, the handle assembly 58 or other, perhaps reusable, components of the delivery device 50 can be omitted and put together prior to use.

The assembly 1 further includes a non-porous container 102 positioned around the implant 10 that is at least partially filled with sterilization fluid 104. To maintain the sterilization fluid 104 within the container 102, a shaft seal 106, such as an O-ring or the like, is provided between an opening 110 in the container 102 and the shaft assembly 54. The container 102 and delivery device 50 are housed in a sealed pouch 108 provided in an optional tray 112 that can be at least partially sterilized via "dry" sterilization techniques. The "dry" sterilization techniques disclosed herein, include, but are not limited to, gas-based techniques known in the art such as ethylene oxide (EtO). Therefore, in some embodiments, the sealed pouch 108 is gas-permeable. Such "dry" sterilization techniques also include radiation-based sterilization techniques including, but not limited to electron beam sterilization. In one illustrative embodiment, the sealed pouch 108 is made of flashspun high-density polyethylene fiber. The dry sterilization process, however, will not be capable of stereaelizing the area 114 between the shaft seal 106 and the shaft assembly 54. Unsterile sections of the shaft assembly 54 (e.g., area 114) or the container 102 would make the delivery device 50 unusable as the risk of non-sterile contamination to the end user is expected. Therefore, the assembly 1 further includes a positioning apparatus 120 that can vary the position of the container 102 and the shaft seal 106 with respect to the shaft assembly 54.

The positioning apparatus 120 of this embodiment includes a pin 122 in adjacent the container 102 and extending through a seal housing 124 and out of the sealed pouch 108. Around the pin 122 is a biasing element 126 (e.g., a compression spring having a compression constant of 1,000 Nm) positioned between the container 102 and a seal housing 124. The sealing housing 124 includes a seal 127 to maintain the sealed nature of the sealed pouch 108. The seal housing 124 passes through the tray 112 and is locked in place with a seal housing lock nut 128. To maintain the pin 122 in a first position of FIG. 4A, a release tab 130 is provided, which is configured to maintain the position of the pin 122 against the bias of the biasing element 126. In one example embodiment, the release tab 130 can be a slotted U-shaped component which slots into a groove (not visible) in the pin 122. Upon removal of the release tab 130, the pin 122 can move longitudinally within the seal housing 124 with the bias of the biasing element 126 to the position of FIG. 4B. In this way, the container 102, including the shaft seal 106, is pushed proximally along the shaft assembly 54 to a second position that is proximal with respect to the first position of FIG. 4A (i.e. proximal with respect to the area 114). In this way, following the sterilization of the components of the assembly 1 within the sealed pouch 108 via dry sterilization techniques, the area 114 can then be sterilized with the sterilization fluid 104 present in the container 102 by the proximal movement of the container 102 along the shaft assembly 54.

Alternatively, the biasing element 126 can be a tension spring (having a constant of 1,000 Nm). In this embodiment, upon release of the release tab 130, the container 102 is pulled distally via the biasing element 126. The unsterilized area 114 in FIG. 4A can then be sterilized with the components of the assembly 1 within the sealed pouch 108 via dry sterilization techniques when displaced into a dry sterilization zone as generally defined by the area within the sealed pouch 108 that is outside of the container 102.

Figure 5:
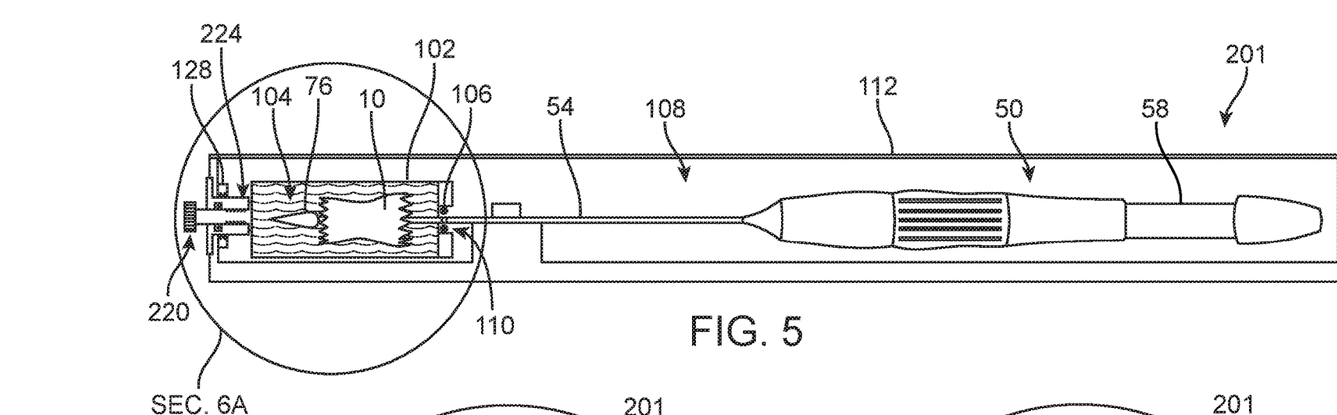
FIG. 5 is a schematic illustration of an alternate assembly in a first position.
Figure 6A:
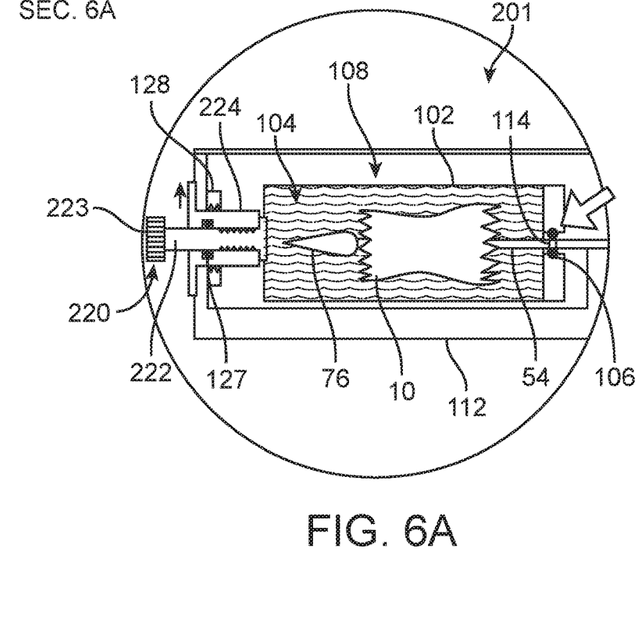
FIG. 6A is an enlarged view of Section 6A of FIG. 5.
Figure 6B:
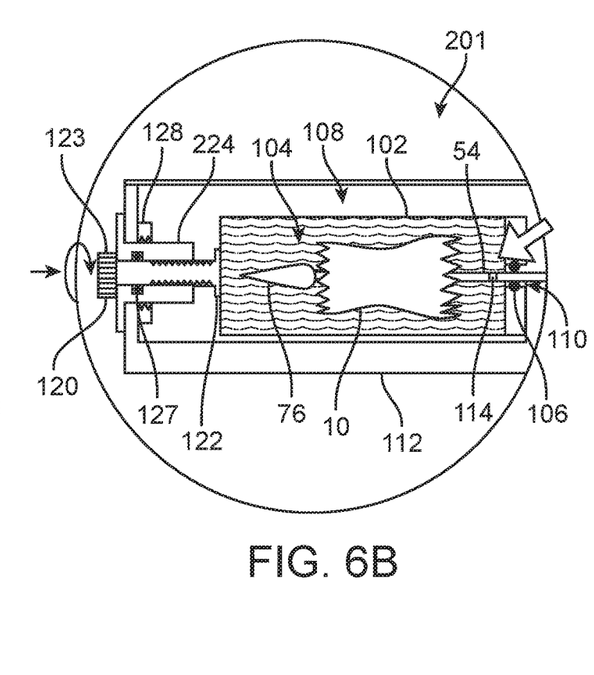
FIG. 6B is an enlarged view of Section 6A of the assembly in a second position.

Referring now also to FIGS. 5-6B, which illustrate an alternate assembly 201 in which like elements share like reference numbers with previously disclosed embodiments and which is identical to the assembly 1 of FIGS. 3-4B except as explicitly stated. This assembly 201 includes a seal housing 224 maintaining seal 127 and is threadably engaged with a positioning apparatus 220. The positioning apparatus 220 includes a pin 222 having a knob 223 located outside of the tray 112. Rotation of the knob 223 longitudinally translates the pin 222 perpendicular to the seal housing 224, thus correspondingly pushing the container 102 (including the shaft seal 106) in a proximal direction away from the seal housing 224. The pin 222 can be configured to be fixed to the container 102 to prevent disconnection of the pin 222 from the container 102 but to allow rotary movement of the pin 222. In such embodiments, the assembly 201 is dry sterilized prior to the container 102 being moved proximally to the second position to expose area 114 with respect to the shaft seal 106 to the sterilization fluid 104. In alternate embodiments, the positioning apparatus 220 can be configured to pull the container 102 distally into the second position. In such embodiments, the area 114 can be sterilized via dry sterilization techniques once the container 102 has been moved distally to the second position to expose area 114 with respect to the shaft seal 106.

Figures 7, 8A, 8B:
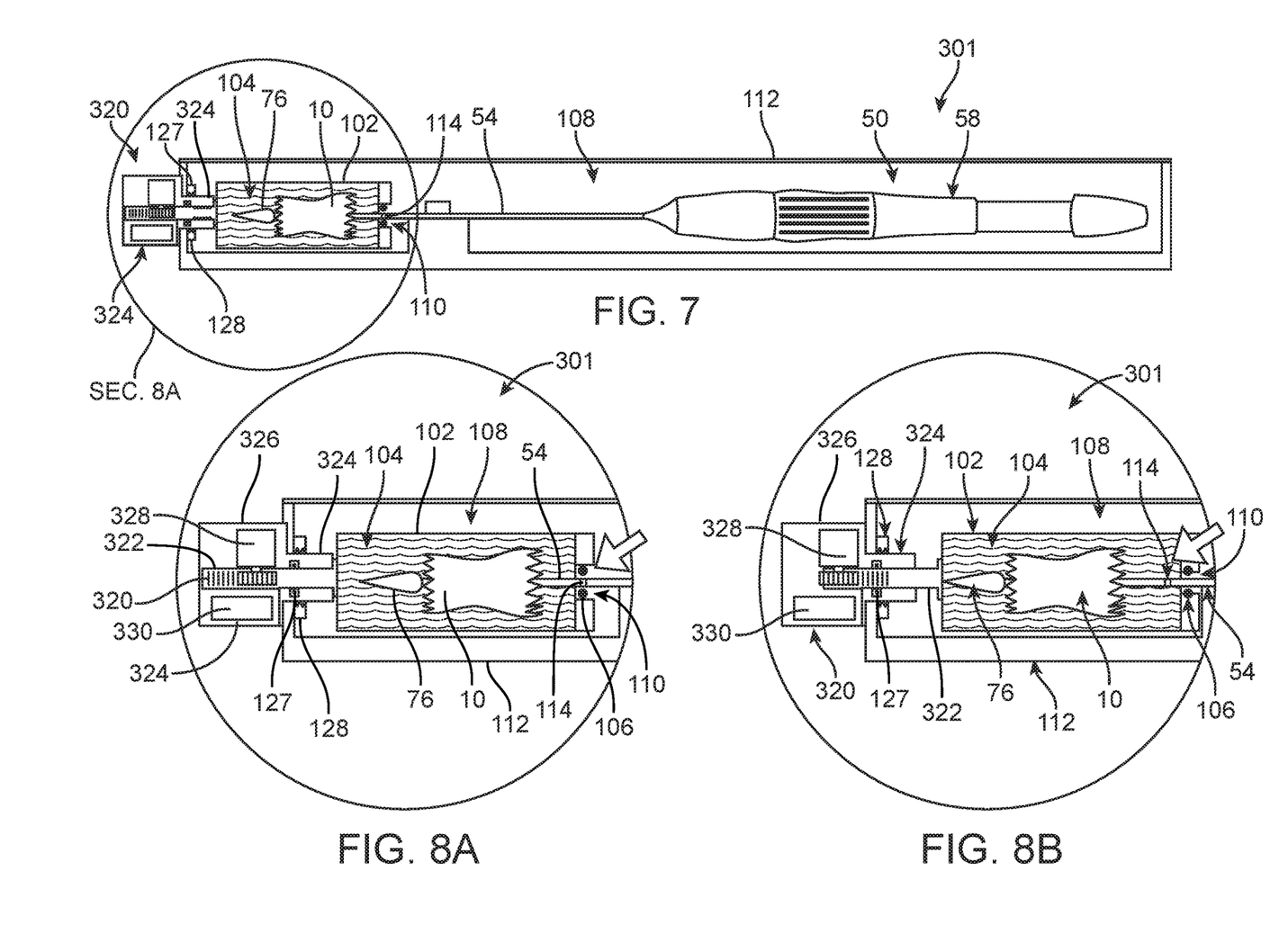
FIG. 7 is a schematic illustration of yet another assembly in a first position.
FIG. 8A is an enlarged view of Section 8A of FIG. 7.
FIG. 8B is an enlarged view of Section 8B of the assembly in a second position.

Referring now also to FIGS. 7-8B, which illustrate an alternate assembly 301 in which like elements share like reference numbers with previously disclosed embodiments and which is identical to the assembly 1 of FIGS. 3-4B except as explicitly stated. As with prior described embodiments, this assembly 301 includes a positioning apparatus 320 having a pin 322 interfacing with the container 102 and extending through a seal housing 324 and exterior to the sealed pouch 108. To actuate movement of the pin 322 and the container 102 along the shaft assembly 54, the positioning apparatus 320 includes a motor assembly 326 engaged with the pin 322 in a rack and pinion arrangement. The motor assembly 326 includes a motor 328 and a control circuit with battery 330, which are optionally assembled to the seal housing 324. The motor assembly 326 can be manually actuated or can alternatively be controlled via a timer (provided in the control circuit) to automatically move the pin 322 to push the container 102 proximally with respect to the shaft assembly 54 to correspondingly move the shaft seal 106 proximally. If the shaft seal 106 is moved proximally, area 114 can be sterilized via the sterilization fluid 104 within the container 102. Alternatively, it is envisioned that the motor assembly 326 could be positioned within the sealed pouch 108 and also that the motor assembly 326 and pin 322 could be configured to pull the container 102 in a distal direction toward the seal housing 324 along the shaft assembly 54. If the shaft seal 106 is moved distally, the area 114 can then be sterilized via dry sterilization techniques. If the shaft seal 106 is moved proximally along the shaft, the assembly 301 is first sterilized via dry sterilization techniques.

Figure 9:
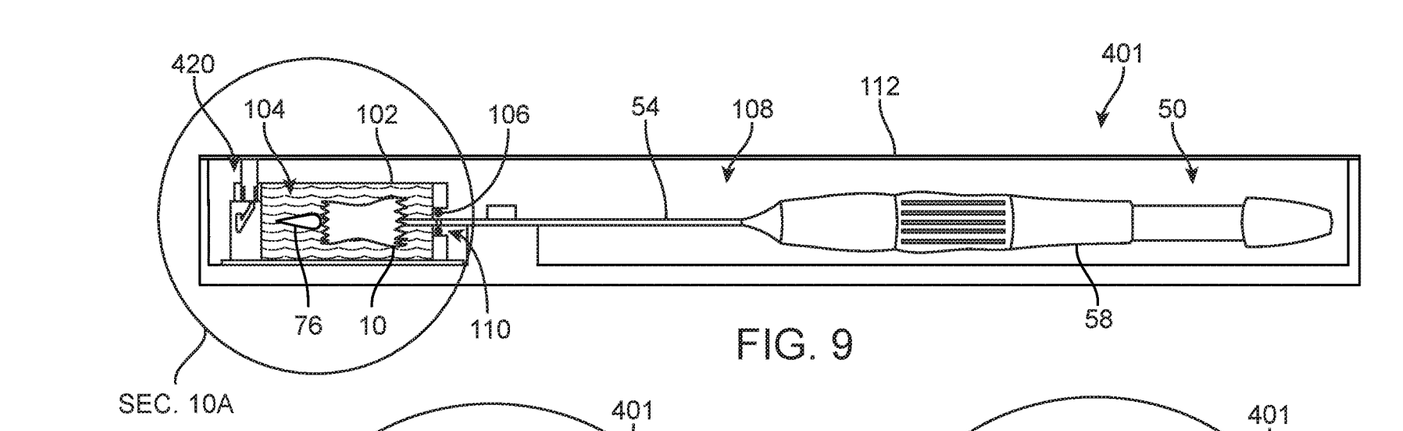
FIG. 9 is a schematic illustration of an alternate assembly in a first position.
Figure 10A:
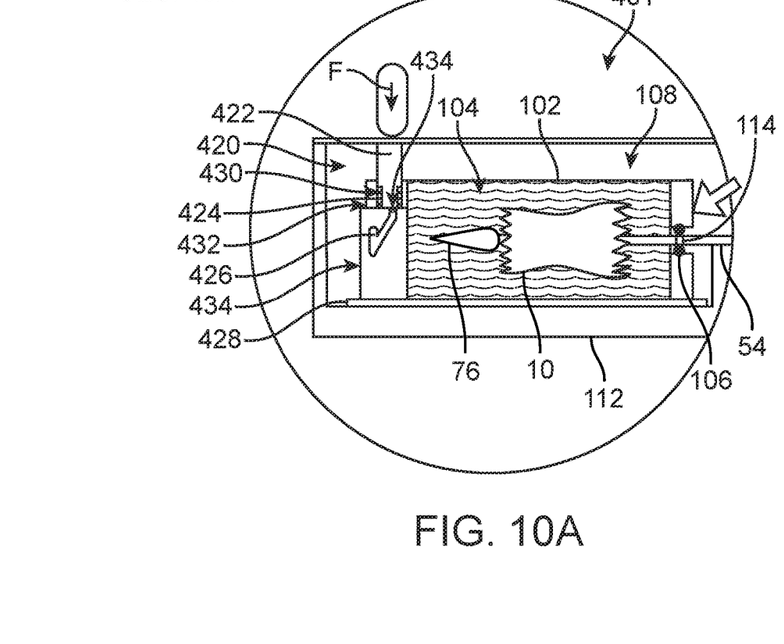
FIG. 10A is an enlarged view of Section 10A of FIG. 9.
Figure 10B:
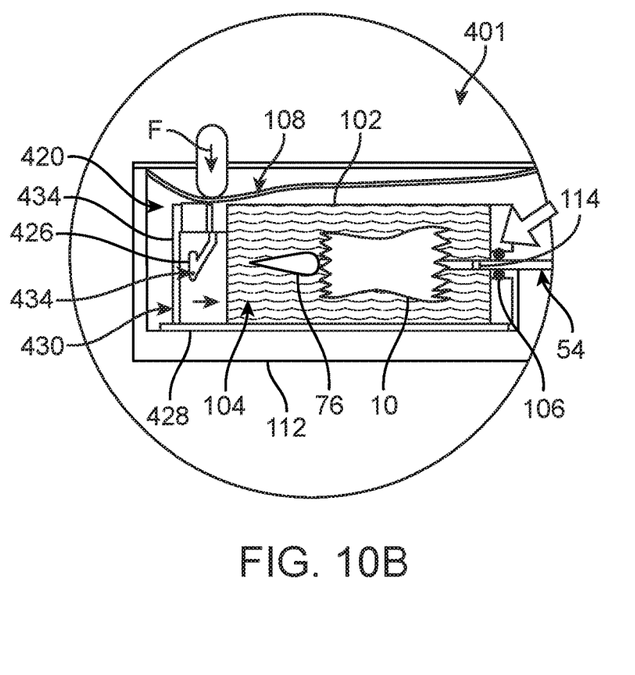
FIG. 10B is an enlarged view of Section 10B of the assembly in a second position.

Referring in addition to FIGS. 9-10B, which illustrate an alternate assembly 401 in which like elements share like reference numbers with previously disclosed embodiments and which is identical to the assembly 1 of FIGS. 3-4B except as explicitly stated. The assembly 401 includes a positioning apparatus 420 provided inside the sealed pouch 108. The positioning apparatus 420 of this embodiment includes a push pin 422 positioned within a cam slide 430. The push pin 422 is biased to the position of FIG. 10A with a compression spring 424 or the like.

To actuate movement of the container 102 with respect to the shaft assembly 54 following the dry sterilization of assembly 401 within the sealed pouch 108, a user pushes the displacement pin 422, with their finger, for example, through the flexible, sealed pouch 108 to create a force F. The push pin 422 actuates a cam slide 430 so that as the push pin 422 is pressed, the container 102 is displaced, thus moving the unsterile area 114 into the sterilization fluid 104 within the container 102 and subsequently sterilizing the area 114. The positioning apparatus 420 can include a platform 428 on which a cam block 434 of the positioning assembly 420 can move as can be seen in a comparison of FIGS. 10A and 10B. In one illustrative embodiment, the push pin 422 includes a mating feature 434, which engages a cam slot 426 within the cam block 434. When force F is released from the push pin 422, the spring 424 pushes the push pin 422 upwards and the push pin 422 engages the cam slot 426 ("cam locking position"). Once the push pin 422 is in the cam locking position, the container 102 is fixed in the position of FIG. 10B. Alternatively, the push pin 422 can be configured to move the container 102 distally along the shaft assembly 54 thereby moving the unsterile area 114 into a dry sterilization zone generally defined as the area within the sealed pouch 108 and outside of the container 102. In such an embodiment, the area 114 can be sterilized with dry sterilization techniques once the container 102 and shaft seal 106 are moved to the second position.

Figure 11A:
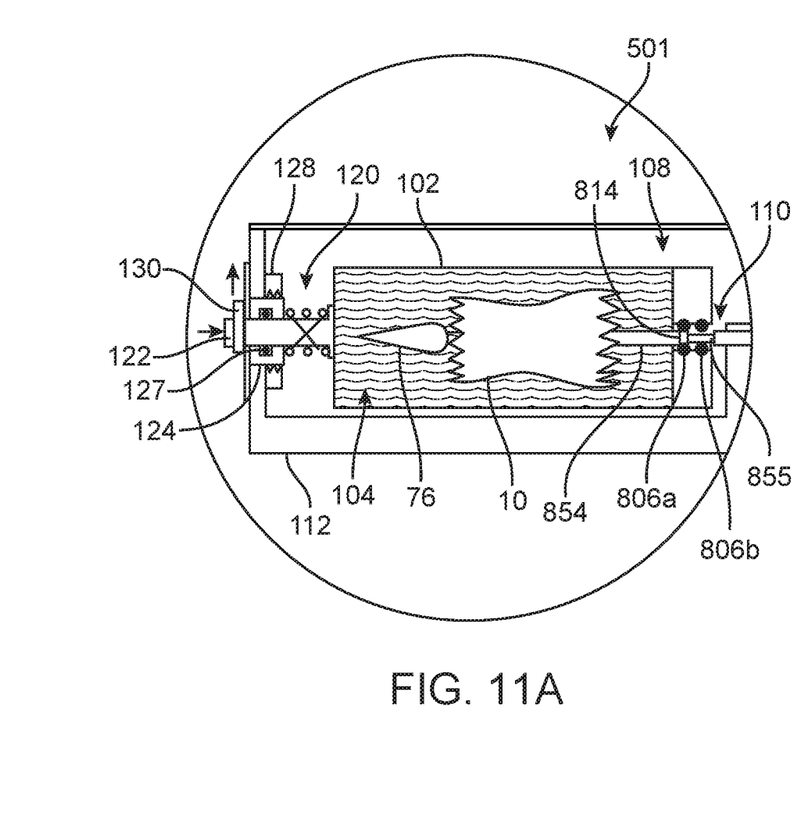
FIG. 11A is a partial, schematic illustration of an alternate assembly in a first position.
Figure 11B:
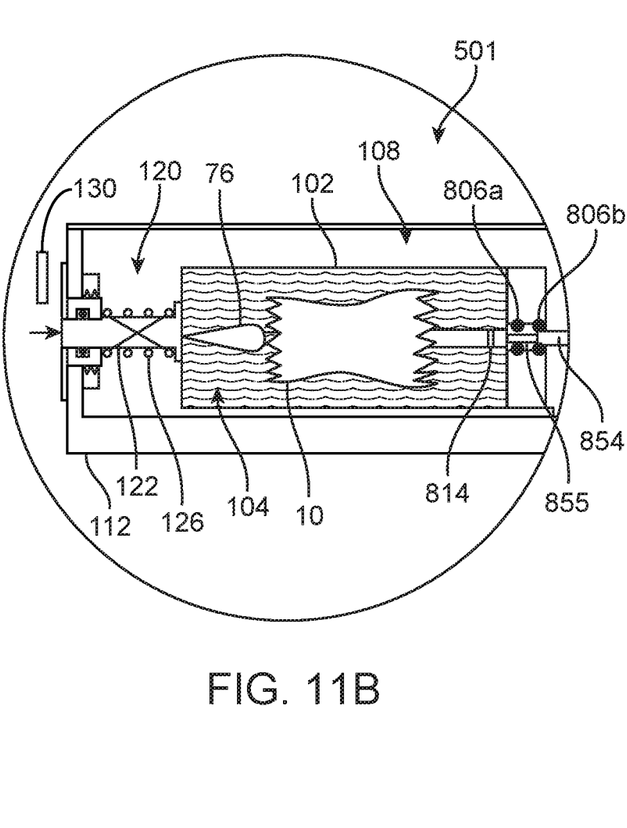
FIG. 11B is a partial, schematic illustration of the assembly of FIG. 11A in a second position.

Referring in addition to FIGS. 11A-11B, which illustrate select components of an alternate assembly 501 in which like elements share like reference numbers with previously disclosed embodiments and which is identical to the assembly 1 of FIGS. 3-4B except as explicitly stated. The assembly 501 includes two shaft seals 806a, 806b provided in the opening 110 of the container 102 between a shaft assembly 854 and the container 102. Each shaft seal 806a, 806b can be an o-ring or the like. The shaft assembly 854 of this embodiment is largely akin to shaft assembly 54 of FIGS. 2A-3 but further includes a portion of reduced diameter 855. In a first position of FIG. 11A, the first shaft seal 806a is in contact with the shaft assembly 854 and an area 814 of the shaft assembly 854 covered by the first shaft 806a seal is potentially unsterile. As can be seen, an area of the shaft assembly 854 proximal to the first seal 806a can be sterilized via dry sterilization techniques as the second seal 806b is not contacting or covering the shaft assembly 854. After dry sterilization, any of the above disclosed positioning apparatuses (120, 220, etc.) can be used to move the position of the container 102 along the shaft assembly 854. As one example, the positioning apparatus 120 of FIGS. 3-4B can be utilized. In this example, the release tab 130 can be disengaged from the pin 122 so that the biasing element 126 pushes the container 102 proximally with respect to the shaft assembly 854. The container 102 moves away from the seal housing 124 and the second seal 806b moves from a disengaged position over the portion of reduced diameter 855 (FIG. 11A) to a second position (FIG. 11B) in which the second seal 806b forms a seal between the container 102 and the shaft assembly 854 while the first seal 806a disengages the shaft assembly 854 and is positioned over the portion of reduced diameter 855. The sterilization fluid 104 is then in contact with the area 814 where the first seal 806a contacted the shaft assembly 854 in the position of FIG. 11A. If the positioning apparatus is one that pulls the container 102 and shaft seals 806a, 806b distally into the second position, dry sterilization techniques can be used to sterilize the area 114. The first and second shaft seals 806a, 806b in combination of the shaft assembly 854 of FIGS. 11A-11B can be utilized in any of the embodiments disclosed herein in a similar manner.

Although the present disclosure has been described with reference to preferred embodiments, workers skilled in the art will recognize that changes can be made in form and detail without departing from the spirit and scope of the present disclosure.

What is claimed is:

1. An assembly comprising:
   a sealed pouch;
   a first portion of a delivery device supporting an implant in the sealed pouch;
   a container housing sterilization fluid, the implant and at least part of the first portion of the delivery device; wherein the container includes an opening and a first shaft seal positioned in the opening and against the first portion of the delivery device; and
   a positioning apparatus; wherein the positioning apparatus is configured to move the container along the first portion of the delivery device.

2. The assembly of claim 1, wherein the positioning apparatus includes a biasing element.

3. The assembly of claim 2, wherein the biasing element is a tension spring.

4. The assembly of claim 2, wherein the biasing element is a compression spring.

5. The assembly of claim 1, wherein the positioning apparatus includes a pin extending from the container to an exterior of the sealed pouch.

6. The assembly of claim 1, wherein the positioning apparatus includes a release tab; further wherein removal of the release tab from the assembly actuates movement of the container.

7. The assembly of claim 1, wherein the positioning apparatus includes a pin.

8. The assembly of claim 7, further comprising a seal housing and the pin is threadably connected with the seal housing; wherein rotational movement of the pin actuates movement of the container.

9. The assembly of claim 7, wherein movement of the pin is controlled via a motor assembly.

10. The assembly of claim 9, wherein the motor assembly includes a control circuit having a timer; wherein the timer is configured to automatically actuate the motor assembly to move the pin.

11. The assembly of claim 1, wherein the positioning apparatus includes a push pin that can be pressed by a user to displace a cam slider which correspondingly displaces the container and moves the container along the first portion of the delivery device.

12. The assembly of claim 11, wherein the push pin is positioned within a cam slider; wherein the push pin includes a mating feature that engages a cam block positioned adjacent the container.

13. The assembly of claim 12, wherein the mating feature engages a cam slot within the cam block.

14. The assembly of claim 12, wherein the positioning apparatus includes a platform on which a cam block of the positioning assembly can move.

15. The assembly of claim 1, wherein the positioning apparatus is configured to move the container proximally with respect to the first portion of the delivery device.

16. The assembly of claim 1, wherein the positioning apparatus is configured to move the container distally with respect to the first portion of the delivery device.

17. The assembly of claim 1, further comprising a second shaft seal proximate the opening of the container.

18. The assembly of claim 17, wherein the first portion of the delivery device includes a portion of reduced diameter.

19. The assembly of claim 18, wherein, in a first position of the container, the second seal is positioned around the portion of reduced diameter and in a second position of the container, the first shaft seal is positioned around the portion of reduced diameter.

20. The assembly of claim 1, wherein the container is housed in the sealed pouch.

* * * * *